United States Patent
Klutts

(10) Patent No.: US 11,752,016 B2
(45) Date of Patent: *Sep. 12, 2023

(54) LINER FOR ORTHOPEDIC OR PROSTHETIC DEVICE

(71) Applicant: Ossur Iceland ehf, Reykjavik (IS)

(72) Inventor: Zachariah J. Klutts, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 338 days.

This patent is subject to a terminal disclaimer.

(21) Appl. No.: 16/538,005

(22) Filed: Aug. 12, 2019

(65) Prior Publication Data

US 2019/0358062 A1 Nov. 28, 2019

Related U.S. Application Data

(63) Continuation of application No. 15/787,972, filed on Oct. 19, 2017, now Pat. No. 10,390,976, which is a
(Continued)

(51) Int. Cl.
*A61F 2/78* (2006.01)
*A61F 5/30* (2006.01)
(Continued)

(52) U.S. Cl.
CPC .............. *A61F 2/7812* (2013.01); *A61F 5/01* (2013.01); *A61F 5/0123* (2013.01); *A61F 5/30* (2013.01);
(Continued)

(58) Field of Classification Search
None
See application file for complete search history.

(56) References Cited

U.S. PATENT DOCUMENTS

| 937,478 A | 10/1909 | Sims |
| 1,328,541 A | 1/1920 | Palmer |

(Continued)

FOREIGN PATENT DOCUMENTS

| EP | 0397998 A1 | 11/1990 |
| EP | 0611069 A1 | 8/1994 |

(Continued)

OTHER PUBLICATIONS

Article: "Thermoplastic Elastomers TPE, TPR, TPV," 6pp., (visited Mar. 14, 2007)<<http://www.bpf.co.uk/bpfindustry/plastics_materials_thermplasrubber_TPR.cfm>>.

(Continued)

*Primary Examiner* — David H Willse
(74) *Attorney, Agent, or Firm* — Workman Nydegger

(57) ABSTRACT

A liner for an orthopedic or prosthetic device includes a core formed from a porous and compressible material, a first layer secured to the first side of the core and forming a first surface to the liner, and a second layer secured to the second side of the core and forming a second surface to the liner. The first and second layers may comprise different properties from one another and be formed from different materials including fabrics and polymeric materials. A polymeric film may be secured to the core or one of the layers to define at least part of a surface of the liner.

18 Claims, 5 Drawing Sheets

Related U.S. Application Data continuation of application No. 14/996,065, filed on Jan. 14, 2016, now Pat. No. 10,383,747.

(60) Provisional application No. 62/237,012, filed on Oct. 5, 2015, provisional application No. 62/103,678, filed on Jan. 15, 2015.

(51) Int. Cl.
*A61F 5/01* (2006.01)
*A61F 13/06* (2006.01)
*A61F 2/50* (2006.01)
*A61F 13/00* (2006.01)

(52) U.S. Cl.
CPC ....... *A61F 13/06* (2013.01); *A61F 2002/5056* (2013.01); *A61F 2002/785* (2013.01); *A61F 2002/7818* (2013.01); *A61F 2002/7881* (2013.01); *A61F 2005/0172* (2013.01); *A61F 2013/00565* (2013.01); *A61F 2210/0076* (2013.01)

(56) References Cited

U.S. PATENT DOCUMENTS

| | | | |
|---|---|---|---|
| 2,032,923 A | 4/1936 | Eldridge | |
| 2,717,841 A | 9/1955 | Biefeld et al. | |
| 2,935,065 A | 5/1960 | Homier et al. | |
| 3,089,486 A | 5/1963 | Pike | |
| 3,463,147 A | 8/1969 | Stubbs | |
| 3,514,313 A | 5/1970 | Martel et al. | |
| 3,520,765 A | 7/1970 | Bateman | |
| 3,561,436 A | 2/1971 | Gaylord, Jr. | |
| 3,696,810 A | 10/1972 | Gaylord, Jr. | |
| 3,789,842 A | 2/1974 | Froimson | |
| 3,877,426 A | 4/1975 | Nirschl | |
| 3,916,077 A | 10/1975 | Damrau | |
| 3,921,626 A | 11/1975 | Neel | |
| 4,193,395 A | 3/1980 | Gruber | |
| 4,204,532 A | 5/1980 | Lind et al. | |
| 4,269,179 A | 5/1981 | Burton et al. | |
| 4,291,072 A | 9/1981 | Barrett et al. | |
| 4,336,279 A | 6/1982 | Metzger | |
| 4,396,012 A | 8/1983 | Cobiski | |
| 4,472,461 A | 9/1984 | Johnson | |
| 4,746,684 A | 5/1988 | Kuriyama et al. | |
| 4,782,605 A | 11/1988 | Chapnick | |
| 4,856,502 A | 8/1989 | Ersfeld et al. | |
| 4,922,929 A | 5/1990 | DeJournett | |
| 4,989,593 A | 2/1991 | Campagna et al. | |
| 4,991,574 A | 2/1991 | Pocknell | |
| 5,154,682 A | 10/1992 | Kellerman | |
| 5,322,729 A | 6/1994 | Heeter et al. | |
| 5,468,219 A | 11/1995 | Crippen | |
| 5,497,513 A | 3/1996 | Arabeyre et al. | |
| 5,540,982 A | 7/1996 | Scholz et al. | |
| 5,635,201 A | 6/1997 | Fabo | |
| 5,769,808 A | 6/1998 | Matthijs et al. | |
| 5,774,902 A | 7/1998 | Gehse | |
| 5,798,165 A | 8/1998 | Mizoguchi et al. | |
| 5,865,776 A | 2/1999 | Springs | |
| 5,916,187 A | 6/1999 | Brill | |
| 5,948,707 A | 9/1999 | Crawley et al. | |
| 5,971,946 A | 10/1999 | Quinn et al. | |
| 6,022,617 A | 2/2000 | Calkins | |
| 6,402,713 B1 | 6/2002 | Doyle | |
| 6,405,731 B1 | 6/2002 | Chiang | |
| 6,592,539 B1 | 7/2003 | Einarsson et al. | |
| 6,656,142 B1 | 12/2003 | Lee | |
| 6,826,641 B2 | 11/2004 | Shindo | |
| 6,861,379 B1 | 3/2005 | Blaszczykiewicz | |
| D519,637 S | 4/2006 | Nordt et al. | |
| D519,638 S | 4/2006 | Nordt et al. | |
| D520,141 S | 5/2006 | Nordt et al. | |
| D521,644 S | 5/2006 | Nordt et al. | |
| 7,169,720 B2 | 1/2007 | Etchells et al. | |
| 7,303,539 B2 | 12/2007 | Binder et al. | |
| 7,762,973 B2 | 7/2010 | Einarsson et al. | |
| 8,267,879 B2 | 9/2012 | Ingimundarson et al. | |
| 10,390,976 B2 * | 8/2019 | Klutts | A61F 5/01 |
| 2001/0001351 A1 | 5/2001 | Dieckhaus | |
| 2002/0132086 A1 | 9/2002 | Su-Tuan | |
| 2004/0058102 A1 | 3/2004 | Baychar | |
| 2005/0010155 A1 | 1/2005 | Chiang et al. | |
| 2006/0015980 A1 | 1/2006 | Nordt, III et al. | |
| 2006/0020237 A1 | 1/2006 | Nordt, III et al. | |
| 2006/0026732 A1 | 2/2006 | Nordt, III et al. | |
| 2006/0026733 A1 | 2/2006 | Nordt, III et al. | |
| 2006/0026736 A1 | 2/2006 | Nordt, III et al. | |
| 2006/0030802 A1 | 2/2006 | Nordt, III et al. | |
| 2006/0030803 A1 | 2/2006 | Nordt, III et al. | |
| 2006/0030804 A1 | 2/2006 | Nordt, III et al. | |
| 2006/0030805 A1 | 2/2006 | Nordt, III et al. | |
| 2006/0030806 A1 | 2/2006 | Dordt, III et al. | |
| 2006/0070164 A1 | 4/2006 | Nordt, III et al. | |
| 2006/0070165 A1 | 4/2006 | Nordt, III et al. | |
| 2011/0208101 A1 | 8/2011 | Keller et al. | |
| 2012/0078154 A1 * | 3/2012 | Pigg | A61L 15/425 602/46 |
| 2013/0035770 A1 | 2/2013 | Egilsson et al. | |

FOREIGN PATENT DOCUMENTS

| | | |
|---|---|---|
| WO | 0070984 A1 | 11/2000 |
| WO | 2010099130 A1 | 9/2010 |
| WO | 2013001083 A1 | 1/2013 |

OTHER PUBLICATIONS

Advertisement: "Custom Engineered Fabrics and Products for Advanced High Performance," 1p., Gehring Textiles (visited Dec. 15, 2005) <<http://www.gehringtextiles.com/d3.html>>.

Brochure: "CTI Custom Ligament Knee Braces," (visited Jan. 7, 2016) <<www.ossur.com>> 1 page.

* cited by examiner

LINER FOR ORTHOPEDIC OR PROSTHETIC DEVICE

FIELD OF THE DISCLOSURE

The disclosure relates to a liner for orthopedic or prosthetic devices, and to a liner structure including a core formed from a porous and compressible material, a breathable first layer and a second layer formed from a polymeric emulsion having vapor permeability and improved frictional characteristics.

BACKGROUND

Liners including vapor permeability and frictional characteristics exist for orthopedic and prosthetic devices and serve as a padded interface between an orthopedic or prosthetic device and skin of a user. While these liners exist, many must compromise vapor permeability and frictional characteristics due to the limitations of materials involved. These solutions must balance the costs of materials used, their characteristics, and the processes employed for making the liners. Few solutions have been able to produce a liner that is low-cost, simple to manufacture, and possesses suitable characteristics including breathability, compressibility or padding, and desirable frictional properties.

SUMMARY

The liner embodiments described may be used in a variety of prosthetic or orthopedic applications. The liner embodiments may also be provided with no relationship to a particular prosthetic or orthopedic device, and used in a variety of applications where frictional control, breathability, compression or padding is required or desired.

An embodiment of the liner preferably includes a compressible core and a second layer formed by a polymeric or polyurethane emulsion. The core possesses greater rigidity than the second layer, and both the core and second layer enable a transfer of air and vapor through their combined thickness. Both the core and the second layer are compressible, and the second layer preferably has enhanced frictional properties to inhibit sliding against a user's skin when sweat is present. The second layer has a fine porous structure enabling vapor transmission, while also having a compressible thickness for providing padding.

In variations of the compressible core, additional layers of foam or similar compressible materials may be used having different rigidities so the liner can be tailored over its length to different levels of compressibility depending on its intended application.

A first layer, such as a hook-receivable material, may be secured to a first surface of the core on a side opposite to a second side of the core with the second layer. The first layer may extend over the entire first surface of the core and may be laminated to the core or otherwise adhered to the core to prevent separation therefrom.

Variations of the second layer may include a plurality of apertures besides the inherent porous structure of the second layer. The plurality of apertures further enhances the breathability of the liner and may be in discrete locations where enhanced breathability is required or may extend over the entire core. The apertures may be formed in a pattern independent of any cell structure or porosity of the core.

The second layer may be formed with varying thicknesses depending on areas requiring greater padding or rigidity as the second layer itself has compressible properties. The different thicknesses may be formed by molding to create different thickness regions, or the second layer may comprise different layers at particular areas to obtain the different thicknesses. The second layer may include areas having different density properties relative to other areas, either with greater or reduced porosity.

A surface of the second layer forms an outer surface of the liner, and may be adapted to desirable frictional properties. The polyurethane emulsion may be modified to have inherent frictional properties suitable for preventing migration along the skin of a user when force is applied regardless of sweat or other skin conditions.

In a variation, the outer surface of the second layer may include a surface pattern that improves friction and breathability of the liner and particularly the second layer. The second layer may include a pattern comprising a plurality of protrusions that space portions of the second layer from the skin of the user, and create air channels between the areas of the second layer without the protrusions and the skin of the user. The protrusions may be arranged to modify the frictional characteristics of the second layer in supplement to the inherent frictional properties of the polyurethane emulsion.

The core may be open-cell foam having a plurality of random pores and cells along the surface thereof, and the second layer inherently has random and substantially small pores located through its thickness irrespective of the pores and cells of the core. The foam of the core and the second layer may comprise a cellular structure that allows them to compress and recover in response to loading or applying the liner onto the anatomy of the user.

A mesh layer may be provided as an interface between the core and the second layer. The mesh layer defines a surface pattern including a plurality of apertures extending through a thickness of the mesh layer. The second layer impregnates the plurality of apertures and extends through at least part of or through the entire thickness of the mesh layer. The surface pattern of the mesh layer can form various channels or recesses that extend only into a partial thickness of the mesh layer such that the second layer extends into the channels or recesses to interlock with the mesh layer. The mesh layer may prevent the second layer from occluding or damaging the foam layer of the core.

The mesh layer is preferably laminated or adhered to the foam layer of the core. The mesh layer is desirably porous and may be substantially more porous than the second layer to avoid inhibiting breathability of the liner. The mesh layer may be substantially thinner than the second layer and the core, and may be formed by a sleeve constructed of a fabric including spandex, lycra, nylon, polyester, microfiber, three-dimensional fabrics, and/or other suitable fabrics.

A third layer may be provided as an interface between the core and the mesh layer. The third layer is substantially thin and is laminated to both the core and the mesh layer.

According to an embodiment, the liner defines a peripheral edge portion defined as a substantially thinned region compared to regions of the liner outside the peripheral edge portion. The peripheral edge portion may be defined as a compressed structure including at least the second layer and the core. Any mesh layer or fabric layers may lack any significant ability to be compressed. The compressed peripheral edge portion may be provided to improve strength of the liner along its edges and channel any vapor transmission through regions bounded by the peripheral edge portion. The peripheral edge portion may include a crimped profile or other various profiles that can be molded through compression of at least the second layer.

A thickness of the liner may vary at least near the peripheral edge portion, and various thicknesses may exist at other desirable locations. The core and various layers of the liner may be formed to various profiles to accommodate corresponding profiles of orthopedic and prosthetic devices.

The liner may have a film layer located and defined along an outer surface of the liner. The film layer may be a polyurethane film having a substantially smooth surface and defined by a plurality of colors and textures selected by a user. The film layer is preferably porous and is breathable. The film layer may be thermoformed to the core and cut into a shape configured to fit the portion where the film color and texture is required. The film layer covers only part of the surface of the liner and islands or portions are provided along the surface of the liner.

Other methods, embodiments, and variations thereof are described in greater detail in the following discussion.

BRIEF DESCRIPTION OF THE DRAWINGS

These and other features, aspects, and advantages of the present invention will become readily apparent and better understood in view of the following description, appended claims, and accompanying drawings.

DETAILED DESCRIPTION OF VARIOUS EMBODIMENTS

Figure 1:
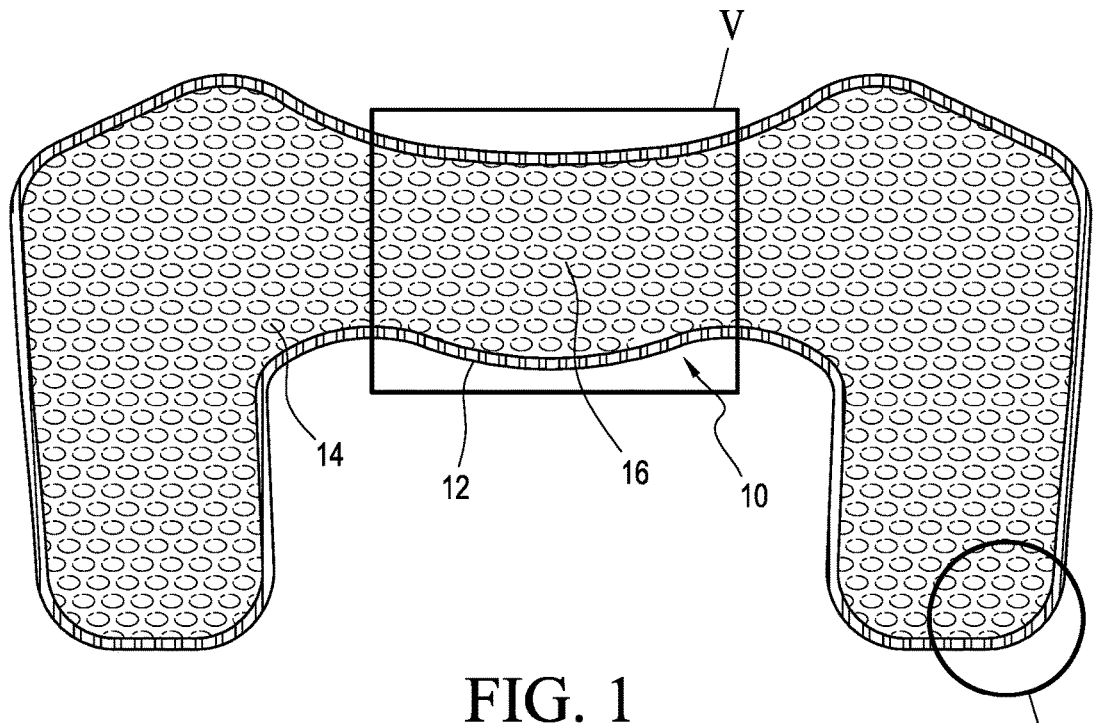
FIG. 1 is a plan view of a liner according to an embodiment of the disclosure.

A better understanding of different embodiments of the invention may be had from the following description read with the accompanying drawings in which like reference characters refer to like elements.

While the disclosure is susceptible to various modifications and alternative constructions, certain illustrative embodiments are shown in the drawings and will be described below. It should be understood, however, there is no intention to limit the disclosure to the embodiments disclosed, but on the contrary, the intention is to cover all modifications, alternative constructions, combinations, and equivalents falling within the spirit and scope of the disclosure and defined by the appended claims.

It will be understood that, unless a term is defined in this patent to possess a described meaning, there is no intent to limit the meaning of such term, either expressly or indirectly, beyond its plain or ordinary meaning.

Referring to the liner embodiment of FIG. 1, the liner 10 defines a profile 12 generally corresponding to a shape of an orthopedic or prosthetic device (not shown). The liner 10 has a side formed by a second layer 14 preferably comprising a polyurethane emulsion. The second layer 14 may form a surface texture 16 molded or created from protrusions of the material forming the second layer 14, as shown in more detail in FIGS. 5A and 5B.

Figure 2:
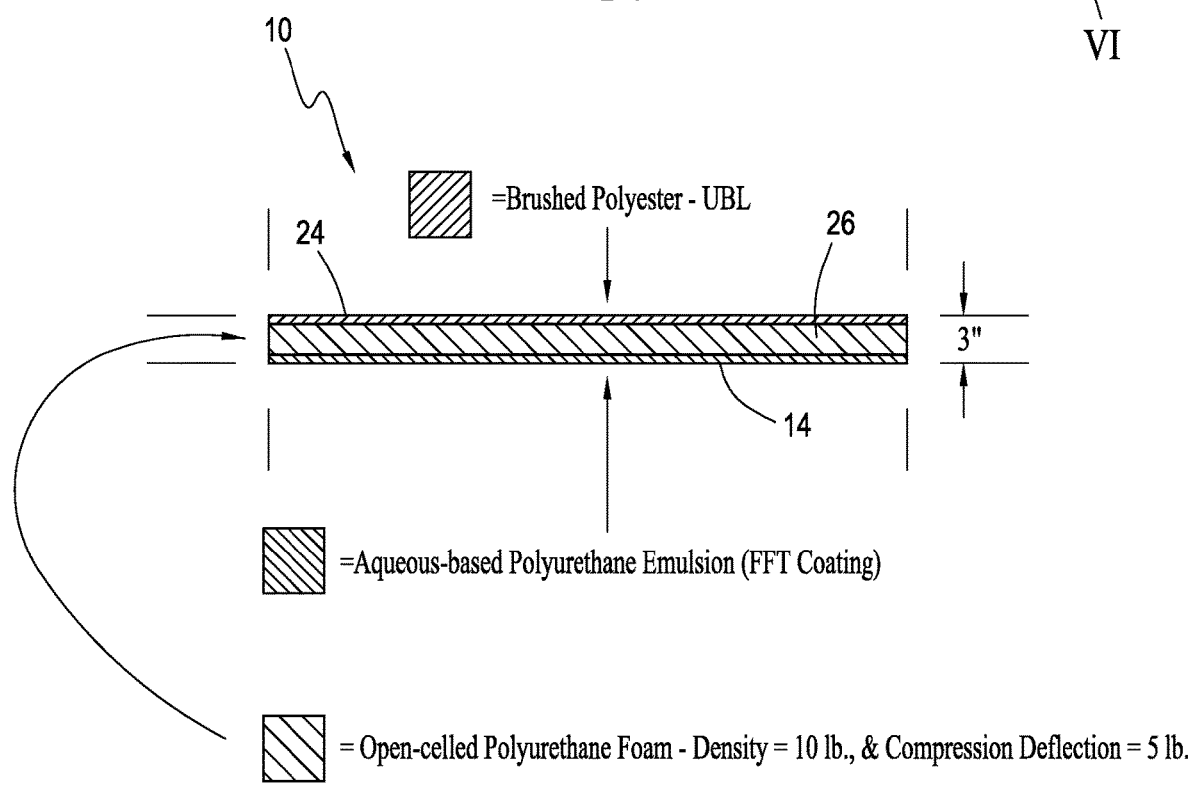
FIG. 2 is a schematic cross-section view of an embodiment of the liner.

FIG. 2 schematically shows a cross-section of an embodiment of the structure of the liner 10. The liner 10 includes a core 26 formed from a porous and compressible material, such as open celled polyurethane foam. The core 26 has first and second sides, with a first layer 24 secured to the first side of the core 26, and a second layer 14 connected to the second side of the core 26. The first layer 24 may be brushed polyester that is a hook receivable material, as in a hook and loop fastener system. The second layer 14 is preferably formed from a polymeric emulsion such that the liner 10 permits a transfer of air and vapor through the first layer 24, the core 26, and the second layer 14.

The core 26 may possess greater rigidity than the second layer 14, and both the core 26 and second layer 14 enable a transfer of air and vapor through their combined thickness. The core 26 and the second layer 14 are compressible and the second layer 14 has enhanced frictional properties such as frictional resistance to forces, that may, for example, inhibit sliding against a user's skin when sweat is present. The second layer 14 has a fine porous structure enabling vapor transmission, while having a compressible thickness providing a layer of padding in supplement to the padding of the core 26.

In variations of the core 26, additional layers of foam (or similar compressible materials) may be used having different rigidities so the liner 10 can be tailored over its length to different levels of compressibility depending on its intended application. The core 26 may be open-cell foam having a plurality of random pores along the surface thereof, and the second layer also has random pores located through its thickness irrespective of the pores of the core 26. The foam of the core 26 and the second layer 14 may have a cellular structure that allows them to compress and recover in response to loading or applying the liner 10 onto anatomy of the user.

The first layer 24 may extend over the entire first side of the core 26 and be laminated to the core 26 or otherwise adhered to the core 26 to prevent separation therefrom. The first layer 24 advantageously can secure to hook material on the corresponding orthopedic or prosthetic device, inhibiting sliding or migration of the liner 10 relative to the device.

Variations of the second layer 14 may include a plurality of apertures besides the inherent porous structure of the second layer 14. The plurality of apertures enhances breathability of the liner 10 and may be in discrete locations where enhanced breathability is required, or they may extend over the entire second side of the core 26. The plurality of apertures may be formed in a pattern and independently of any cell structure or porosity of the core 26.

A surface of the second layer 14 forms an outer surface of the liner 10, and may be adapted to possess desirable frictional properties. The polyurethane emulsion may be modified to have inherent frictional properties suitable for preventing migration along skin of a user when force is applied.

Examples of the polyurethane emulsion forming the second layer 14 are described in at least U.S. Pat. No. 4,746,684, granted May 24, 1988, and U.S. Pat. No. 5,798,165, granted Aug. 25, 1998, and incorporated by reference herein.

Figure 3:
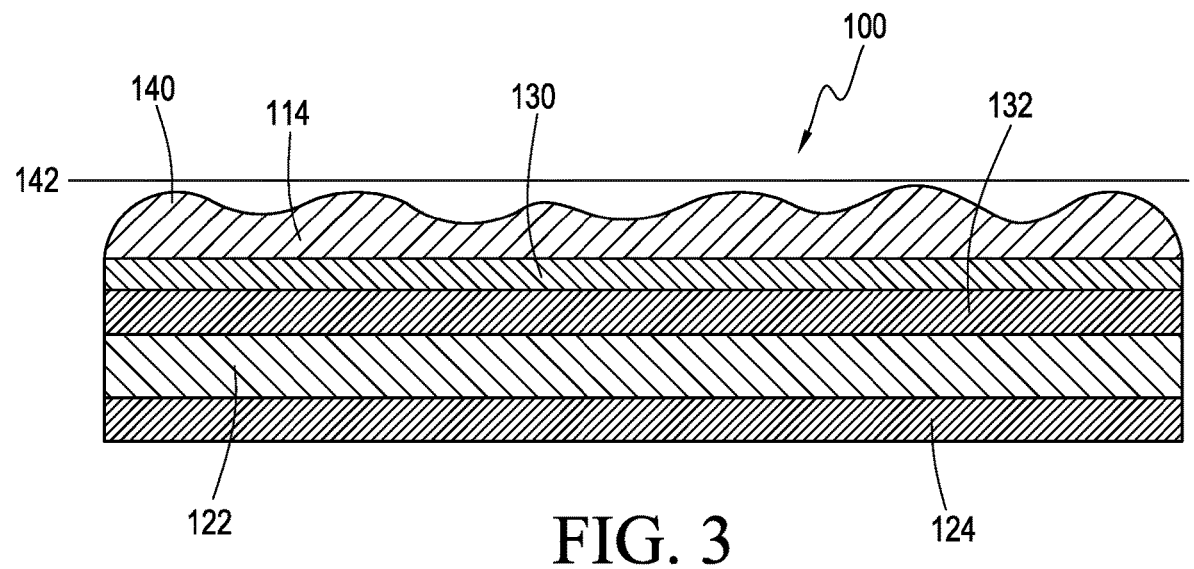
FIG. 3 is a schematic cross-section view of another embodiment of the liner.

FIG. 3 shows another embodiment of liner 100 including different layers to those of the liner 10 of FIG. 2. It will be understood that neither the liner 10 nor the liner 100 must include each of the layers described in connection thereof, but various modifications may be made according to the layers discussed herein. The liner 100 may include a second layer 114 secured to a mesh layer 130. The mesh layer 130 is between the core 122 and the second layer 114, and a third layer 132 may be between the core 122 and the mesh layer 130. As in the liner 10, the liner 100 includes a first layer 124 forming an opposed surface to the surface defined by the second layer 114.

Figure 4:
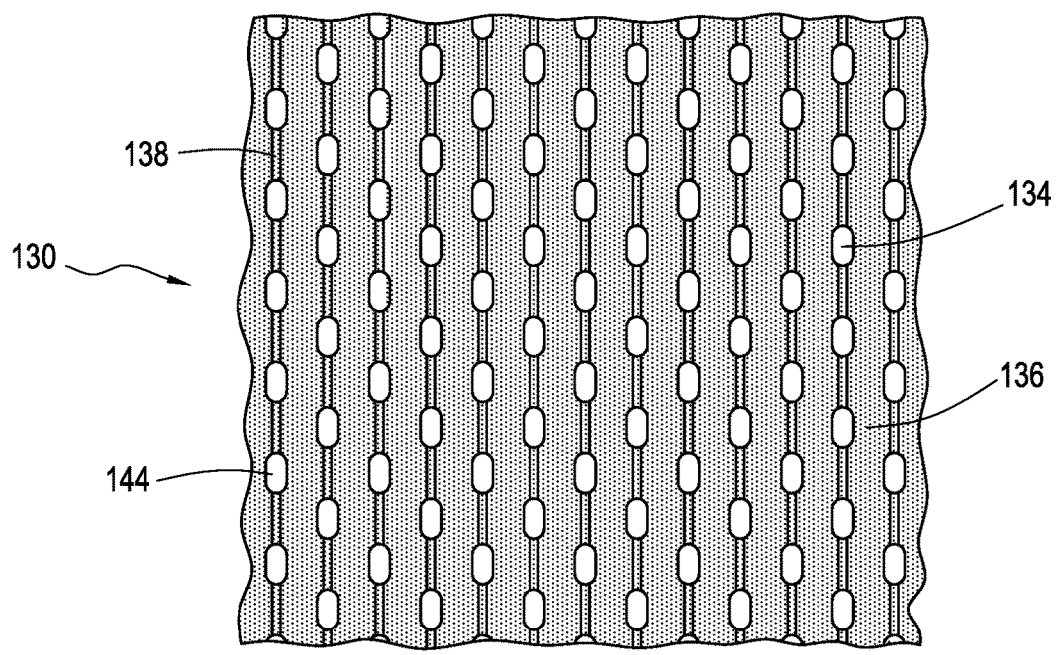
FIG. 4 is a schematic view of the mesh layer of FIG. 3 impregnated with material from a second layer.

As shown in FIG. 4, the mesh layer 130 has a plurality of spaced apertures 134 arranged in a pattern. The second layer 114 may have portions 144 impregnating and interlocking the spaced apertures 134 of the mesh layer 130. The portions 144 extend into the spaced apertures 134 through at least a portion of the thickness of the mesh layer 130, and preferably extend the entire thickness of the mesh layer 130. The mesh layer 130 may also define a plurality of channels or recesses 138 formed along a surface 136 of the mesh layer 130 into which material of the second layer 114 may extend. The channels or recesses 138 preferably only extend within a portion of the mesh layer 130 thickness.

The second layer 114 may be formed with varying thicknesses 140 corresponding to areas requiring greater padding or rigidity as the second layer 114 itself has compressible properties. The thicknesses 140 may vary relative to a baseline 142 defined in FIG. 3 as the maximum thickness. The thicknesses 140 are preferably arranged in a predetermined manner and are distinguished over random variations of thickness due to production methods.

The different thicknesses 140 may be formed by molding at designated locations or the second layer 114 may comprise different layers at particular areas to obtain the different thicknesses 140. The second layer 114 includes areas that can have different density properties relative to other areas, either with greater or reduced porosity.

Figure 5A:
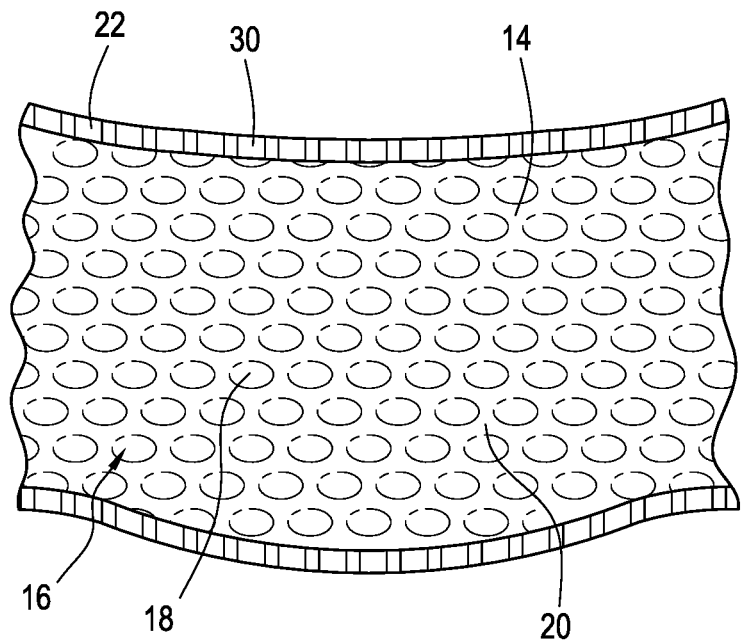
FIG. 5A is a detail view of section V in FIG. 1.
Figure 5B:
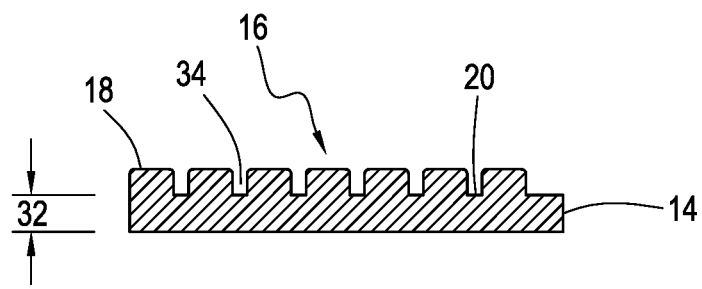
FIG. 5B is a schematic cross-sectional view of the detail view of FIG. 1.

As shown in FIGS. 5A and 5B, the outer surface of the second layer 14 may include a surface pattern 16 that improves friction and breathability of the liner and particularly the second layer 14. The second layer 14 may include a pattern comprising a plurality of protrusions 18 that space portions 20 of the second layer 14 from skin of the user, creating air channels 34 between the areas 20 of the second layer 14 without the protrusions and the skin of the user. The protrusions 18 may be arranged to modify the frictional characteristics of the second layer 14 in supplement to the inherent frictional properties of the polyurethane emulsion. The protrusions 18 preferably extend from a minimum or base thickness 32 of the second layer 14, and are formed continuously with the material forming the second layer 14.

Figure 6:
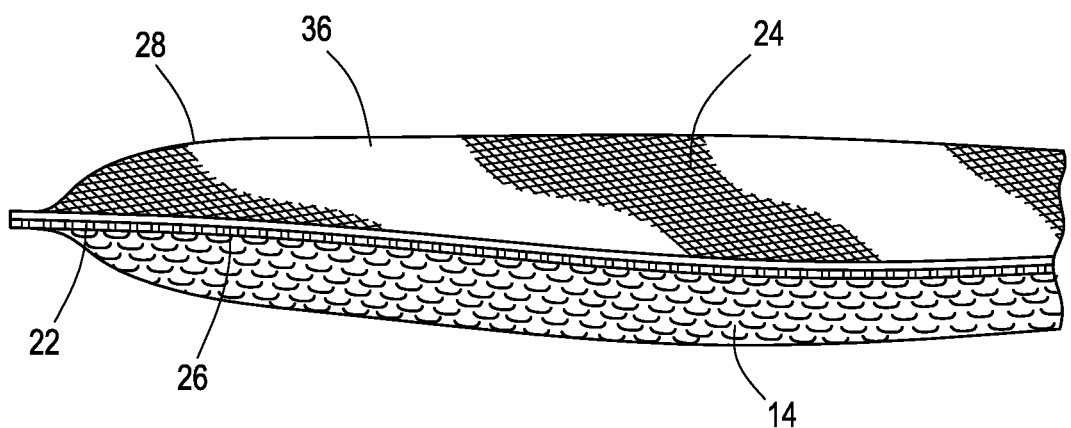
FIG. 6 is a sectional elevational view of section VI in FIG. 1.

FIG. 6 depicts how the liner forms a peripheral edge portion 22 defined as a substantially thinned region compared to regions 36 of the liner outside the peripheral edge portion 22. The peripheral edge portion 22 may be defined as a compressed structure including at least the second layer 14 and the core 26. Any mesh layer or fabric layers may possess varying levels of compressibility or may not be compressible. The peripheral edge portion 22 is adapted to improve the strength of the liner along its edges and channel any vapor transmission through regions bounded by the peripheral edge portion. The peripheral edge portion may include a crimped profile 30 or other profiles molded because of compression of at least the second layer 14.

A thickness 28 of the liner may vary at least near the peripheral edge portion 22, and various thicknesses may be at other desirable locations, as shown in FIG. 3. The core 26 and various layers of the liner may be formed to different profiles to accommodate corresponding profiles of orthopedic and prosthetic devices.

Figure 7:
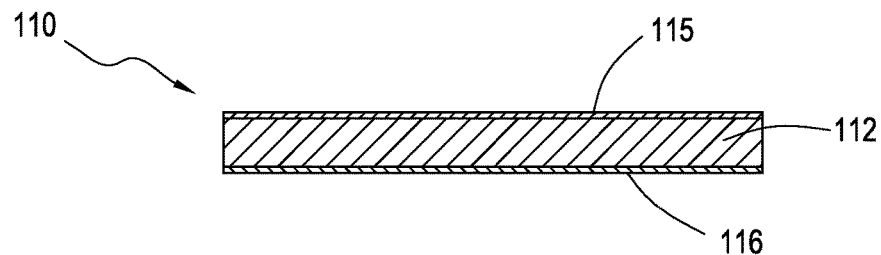
FIG. 7 is a schematic cross-sectional view of a liner structure.
Figure 8:
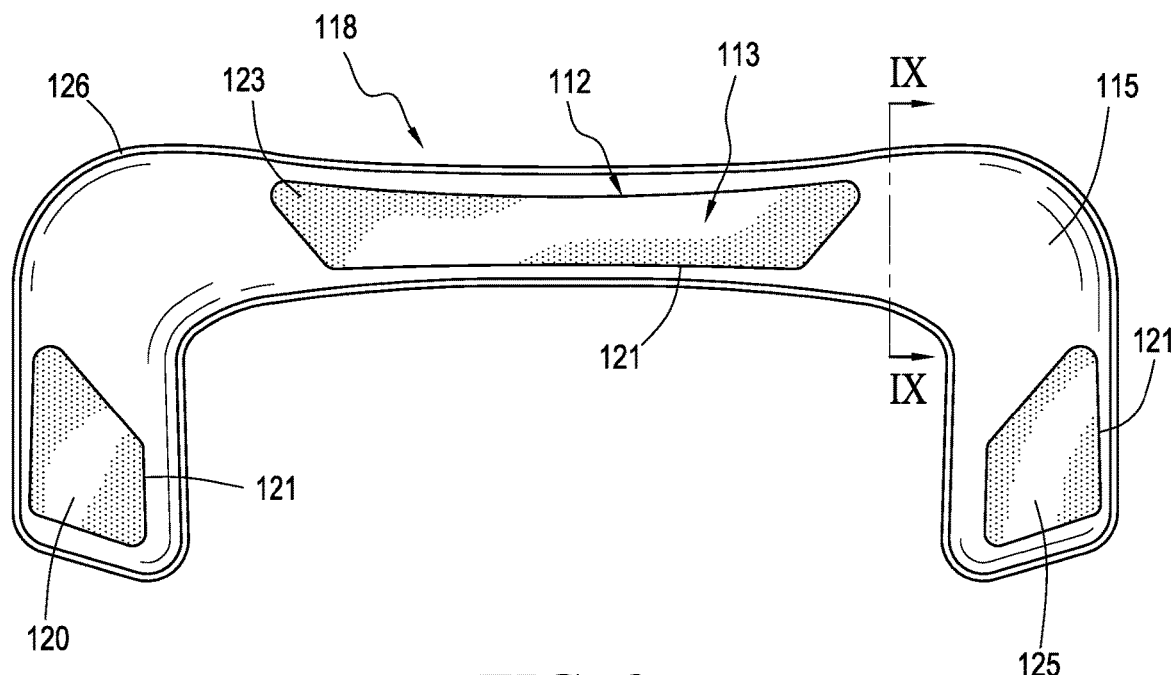
FIG. 8 is a plan view of a liner having a variation of the structure in FIG. 7.
Figure 9:
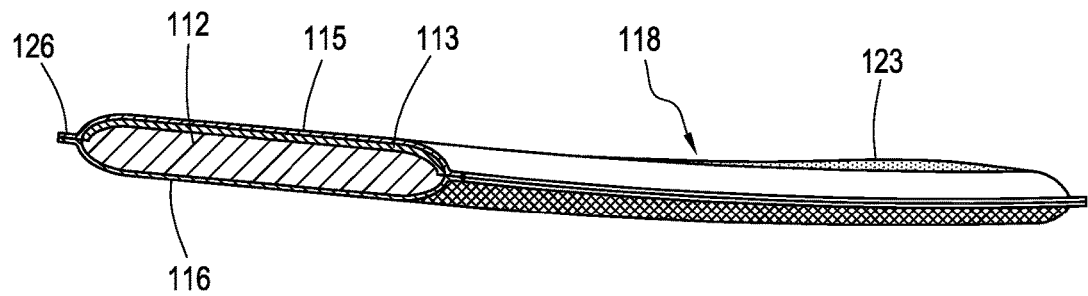
FIG. 9 is a cross-sectional view taken along line IX-IX in FIG. 8.

Turning to the embodiment of FIGS. 7-9, a liner has a structure including a film layer on one of the outer surfaces of the liner. FIG. 7 shows the basic liner structure 110 having a core 112 formed generally as in the liner structure of FIG. 2. The liner structure 110 includes a first layer 116 likewise as in the liner structure of FIG. 2 and forms a first outer surface of the liner structure 110. The first layer 116 is preferably constructed from a hook-receivable or loop material, although it is not limited to such a layer type. The structure 110 further defines a film layer 115 located along a second outer surface of the liner, and may have a color contrast from the first layer 116.

The film layer 115 of the liner allows users to customize the colors of the liner as a whole. While the fabric layer will probably be black, blue, tan or blue in color, as is customary in orthopedic and prosthetic devices, the film can have many contrasting colors selected by the user, including red, green, orange, blue, silver, gold, etc. Such an arrangement may entice the user to wear the orthopedic or prosthetic device after having been able to personalize the color of the liner.

The film layer 115 may be a polyurethane film having a substantially smooth surface and defined by many colors and textures selected by a user. The film layer is preferably porous and is breathable. Examples of the film layer include Bemis OT100, OT260 and OT100RS included and manufactured by Bemis Associates Inc. of Shirley, Mass.

The film layer may be thermoformed to the core and cut into a shape configured to fit the portion where the film color and texture is required. As shown in FIG. 8, the film layer 115 covers only part of the surface of the liner and islands or portions 120, 123, 125 are provided along the surface of the liner 118.

The portions 120, 123, 125 may include a hook receivable material that is thermoformed or laminated to the core 112 specifically at the location or the portions may merely be exposed portions of the core 112. The hook receivable material of the portions 120, 123, 125 may comprise an intermediate layer 113 that extends over an entirety of a surface of the core 112.

The structure of FIG. 7 may be modified such that the hook receivable material is located over the entirety of a second surface of the core 112 and the film layer 115 extends thereover with the hook receivable material between the core 112 and the film layer 115. Alternatively, the intermediate layer 113 may be sub-divided into discrete portions only secured to the core 112 at the areas where the film layer 115 is cut-out to form an opening 121 defining the periphery to the islands or portions 120, 123, 125, only being within the peripheral bounds defined by the film layer 115. If the portions 120, 123, 125 include hook receivable material, they may secure to hook material to engage other features to the liner. The portions 120, 123, 125 may be flush with the film, or may be recessed or raised relative to the film.

The film layer 115 may have a variety of surface textures including a smooth surface, bumps, leather-like texture or grain, dimples, openings or any other suitable surface texture. The surface textures may be arranged to provide enhanced friction against a user's anatomy. The film layer 115 is advantageous in that it may be substantially thin having an exemplary gauge of 0.075 mm, with a range of 0.050 mm to 0.5 mm, and a nominal weight of 90 g/m^2. The film layer 115 is bonded and or laminated to the core 112 and can be bonded and/or pressed to conform to the shape of the core 112, as depicted in FIG. 8 in the liner 118.

FIG. 9 shows the relation of the film layer 115 to the core 112 in that the film layer 115 is substantially thinner than the core 112, although it should be understood the core 112 is not limited to the thickness depicted but can take any thickness desired by a user. The pliability of the film layer 115 enables conforming to the core 112 so as not to impede the function of the liner while enabling selective color and surface texture. The intermediate layer 113 is preferably thicker than the film layer 115 in part due to the preferable construction such as having hook receivable properties. The film layer 115 is substantially thin in part to conform not only to the core 112 but to any three-dimensional shape in which the liner is formed (for example, bending to the shape of an orthopedic or prosthetic device).

FIGS. 8 and 9 show how the edges 126 of the liner 118 may be radio frequency welded to avoid the necessity of stitching or loose edges. The edges 126 of the liner may be tapered, and due to the welding of at least the film layer 115, the intermediate layer 113 and the first layer 116, are integrally formed in that they are inseparable. The edges 126 may form a lip about the periphery of the liner in that the film layer 115 and the first layer 116 extend beyond the core 112 and are substantially compressed to form the edge and encase the core 112. Alternatively, the core 112 may be included in the lip although it is substantially compressed.

The liner may be arranged so a film layer is along both outer surfaces of the liner, thereby covering an entirety or part of the first layer. In this arrangement, the liner can be modified to have a distinctive appearance and selected surface texture according to the film layer. Portions of the first layer may be accessible through the film layer while the film layer surrounds at least a part of these portions.

Figure 10:
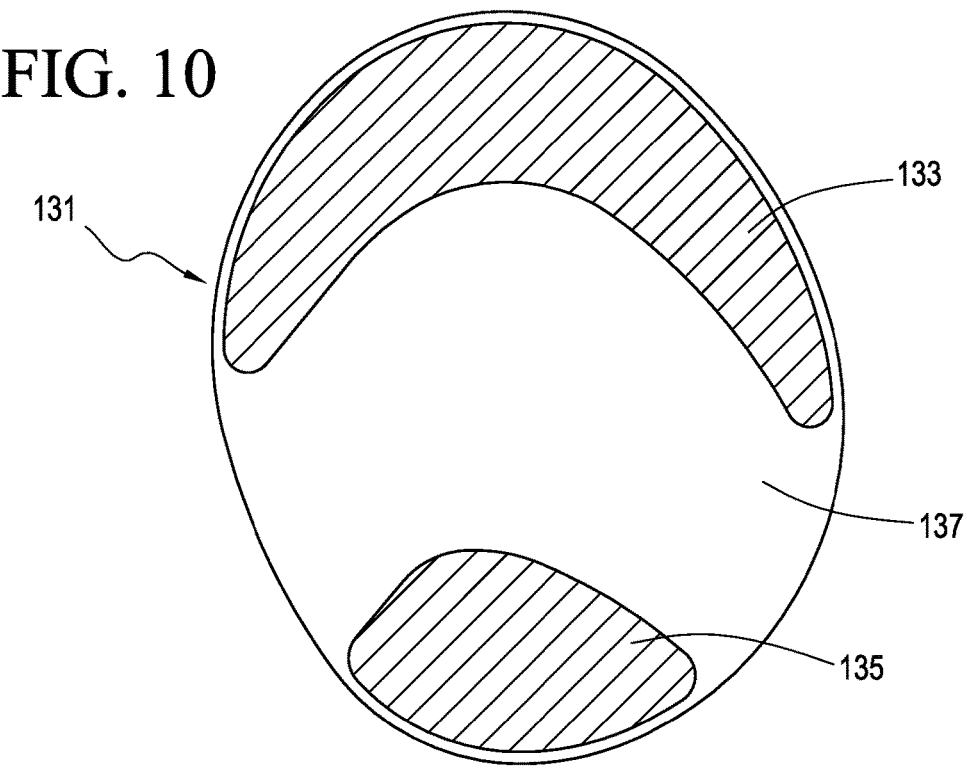
FIG. 10 is a plan view of a liner according to an embodiment of the disclosure.

FIG. 10 shows an example wherein the liner 131 has first and second portions 133, 135 defined along a periphery of the liner 131, and a film layer 137 extends about at least part of the first and second portions 133, 135. This liner 131 may have a thickness greater than the liner in FIGS. 8 and 9 because the liner 131 constitutes a pad for an area of a device requiring greater cushioning or support. Other features may be similar as in aforementioned liner embodiments, e.g. edges, etc.

Because the liners described are breathable, various liner embodiments may be stacked over one another or used in combination with each other. One of the liners might be attached to one feature of a device, whereas another liner is attached to a different feature. The different liners may have different properties such as materials or dimensions for the core and the outer layers.

Figure 11:
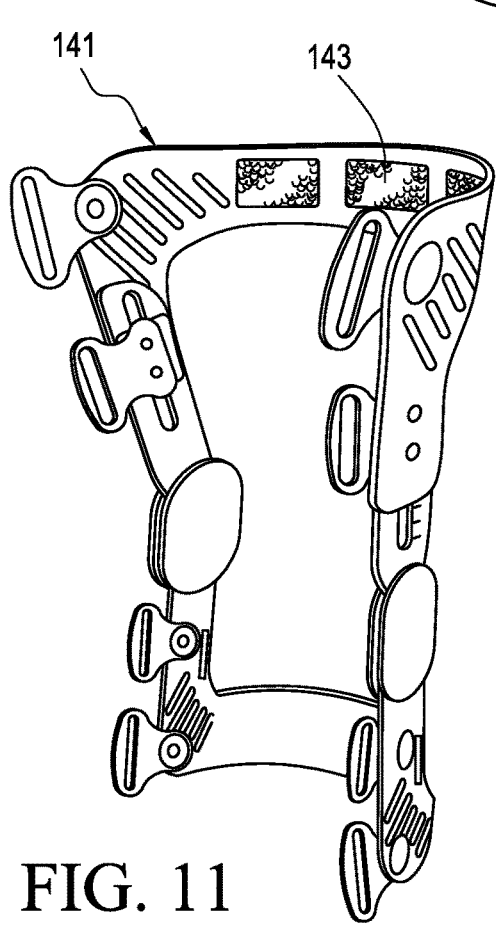
FIG. 11 is a perspective view of an orthopedic device arranged for receiving liners.
Figure 12:
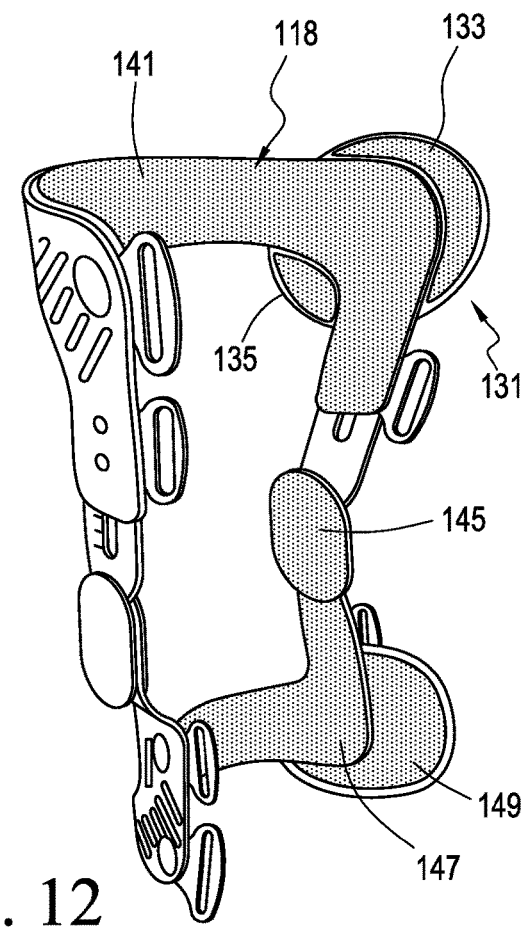
FIG. 12 is a perspective view of the orthopedic device of FIG. 11 including liners.

FIG. 11 shows an orthopedic brace 141 prior to receiving the liners. The brace 141 includes hook material 143 for securing to the first layer of any of the aforementioned liners or any of the aforementioned portions in combination with the film layer. FIG. 12 shows how the liner 118 extends over an inner portion of the brace and extends over the liner 131. The portions 133, 135 of the liner 131 may differ from the outer surface of the liner 118 (i.e., the film layer) according to desired usage of the liner 131 with the contours of the portions 133, 135 accommodating the liner 118.

Other liners may be used having any of the aforementioned features for covering other components of the brace, including hinges and frame components, as shown by pads 145 for the hinges and liners 147, 149 for the frame components. All of the liners may be made to have the same type or different types of film layers. All of the liners may have the same color film layer, such as blue.

It is to be understood that not necessarily all objects or advantages may be achieved under any embodiment of the disclosure. Those skilled in the art will recognize that the liner for an orthopedic or prosthetic device may be embodied or carried out in a manner that achieves or optimizes one advantage or group of advantages as taught without achieving other objects or advantages as taught or suggested.

The skilled artisan will recognize the interchangeability of various disclosed features. Besides the variations described, other known equivalents for each feature can be mixed and matched by one of ordinary skill in this art to construct a liner for an orthopedic or prosthetic device under principles of the present disclosure. It will be understood by the skilled artisan that the features described may be adapted to other types of liners. Hence this disclosure and the embodiments and variations thereof are not limited to orthopedic and prosthetic devices, but can be utilized in any device including a liner.

Although this disclosure describes certain exemplary embodiments and examples of a liner, it therefore will be understood by those skilled in the art that the present disclosure extends beyond the specifically disclosed embodiments to other alternative embodiments and/or uses of the disclosure and obvious modifications and equivalents thereof. It is intended that the present disclosure should not be limited by the particular disclosed embodiments described above.

The invention claimed is:

1. A liner for an orthopedic device, comprising:
  a core formed from a porous and compressible open-celled polyurethane foam, the core having first and second opposite surfaces;
  a first layer formed from an aqueous-based polyurethane emulsion and located along the first surface of the core, the aqueous-based polyurethane emulsion having frictional properties for preventing migration along skin of a user when force is applied to the first layer, wherein the first layer has a fine porous structure enabling vapor transmission, while having a resilient compressible thickness;
  a second layer formed from a hook receivable material and has a first surface located directly adjacent to the second surface of the core, the second layer extending over an entirety of the core and laminated to the second surface of the core, wherein the second layer is a brushed polyester fabric and is vapor transmissible;
  wherein the core has greater rigidity than the first layer, both the core and the first layer are arranged for transfer of air and vapor through a combined thickness.

2. The liner of claim 1, wherein the core and the first layer are compressible.

3. The liner of claim 1, wherein the core has a first plurality of randomly displaced pores along the first surface thereof, the first layer is located directly adjacent to the first surface of the core and has a second plurality of randomly displaced pores located through its thickness irrespective of the first plurality of randomly displaced pores of the core.

4. The liner of claim 1, wherein the core has a cellular structure permitting compression due to a load from a first configuration to a second configuration, and recovery to the first configuration in response to release of the load.

5. The liner of claim 4, wherein the first layer has a cellular structure permitting compression due to the load from the first configuration to the second configuration, and recovery to the first configuration in response to release of the load.

6. The liner of claim 4, further comprising a polymeric film extending over a second surface of the second layer opposite the first surface of the second layer.

7. The liner of claim 6, wherein the polymeric film has a gauge in the range of 0.050 to 0.5 mm, and weight of about 90 g/m^2.

8. The liner of claim 6, wherein the polymeric film is a porous and breathable polyurethane film.

9. The liner of claim 6, wherein the core is substantially thicker than the second layer and the polymeric film.

10. The liner of claim 1, wherein the liner defines tapered peripheral edges, the core being substantially compressed relative to portions of the core outside of the tapered peripheral edges.

11. The liner of claim 10, wherein the first layer extends over an entirety of the first surface of the core including at the tapered peripheral edges.

12. The liner of claim 11, wherein the tapered peripheral edges are welded and devoid of stitching.

13. The liner of claim 11, wherein the first layer is inseparable from the core.

14. The liner of claim 1, wherein the liner defines tapered peripheral edges, the core and the second layer being substantially compressed relative to portions of the core outside of the tapered peripheral edges.

15. The liner of claim 1, wherein the first layer defines a pattern of protrusions extending outwardly therefrom and formed continuously with the first layer.

16. A liner for an orthopedic device, comprising:
a core formed from a porous and compressible open-celled polyurethane foam, the core having first and second surfaces opposite from one another;
a first layer formed from an aqueous-based polyurethane emulsion and located along the first surface of the core, wherein the first layer has a fine porous structure enabling vapor transmission, while having a resilient compressible thickness;
wherein the core has greater rigidity than the first layer, both the core and the first layer are arranged for transfer of air and vapor through a combined thickness;
wherein the core and the first layer are compressible, the first layer having greater frictional properties than the core such as the aqueous-based polyurethane emulsion having frictional properties for preventing migration along skin of a user when force is applied to the first layer;
wherein the first layer defines a pattern of protrusions extending outwardly therefrom and formed continuously with the first layer;
a second layer formed from a hook receivable material and has a first surface located directly adjacent to the second surface of the core, the second layer extending over an entirety of the core and laminated to the second surface of the core, wherein the second layer is a brushed polyester fabric and is vapor transmissible.

17. The liner of claim 16, wherein the liner defines tapered peripheral edges, the core being substantially compressed relative to portions of the core outside of the tapered peripheral edges.

18. The liner of claim 17, wherein the first layer extends over an entirety of the first surface of the core including at the tapered peripheral edges.

* * * * *